United States Patent [19]
Shaw et al.

[11] Patent Number: 5,918,602
[45] Date of Patent: *Jul. 6, 1999

[54] THERAPEUTIC COMPRESSION GARMENT

[75] Inventors: Sandra Anne Shaw, Coronado; Aaron M. Rogers, Solana Beach, both of Calif.

[73] Assignee: Circaid Medical Products, Inc., San Diego, Calif.

[ * ] Notice: This patent is subject to a terminal disclaimer.

[21] Appl. No.: 08/724,991

[22] Filed: Oct. 4, 1996

Related U.S. Application Data

[63] Continuation-in-part of application No. 08/658,519, Jun. 4, 1996, Pat. No. 5,653,244.

[51] Int. Cl.⁶ .................................................. A61F 5/37
[52] U.S. Cl. ................................... 128/882; 602/65
[58] Field of Search ..................... 128/846, 878, 128/879, 882, DIG. 25, DIG. 20; 602/5, 20, 23, 60, 61, 62; 606/200, 201, 202

[56] References Cited

U.S. PATENT DOCUMENTS

| | | | |
|---|---|---|---|
| 3,508,544 | 4/1970 | Moore | 602/65 |
| 3,699,959 | 10/1972 | Garrahan | 602/65 |
| 3,845,769 | 11/1974 | Shaw | |
| 3,934,583 | 1/1976 | Hollingshead | 602/65 |
| 4,215,687 | 8/1980 | Shaw | |
| 5,254,122 | 10/1993 | Shaw | |

*Primary Examiner*—Michael A. Brown
*Attorney, Agent, or Firm*—Harris F. Brotman

[57] ABSTRACT

A therapeutic compression garment made of a unitary piece of flexible, foldable, light weight Velcro-type loop fabric having a central region for wrapping partially around a body part and a plurality of pairs of bands integrally connected to the central region and extending outwardly in opposite directions from both sides of the central region to encompass the body part. The therapeutic garment adapted for the leg in combination with an ankle-foot wrap for applying therapeutic compression to the leg, ankle and foot. A method for treating disorders requiring compressive therapy involving the step of applying the garments of the invention to the indicated body part.

33 Claims, 10 Drawing Sheets

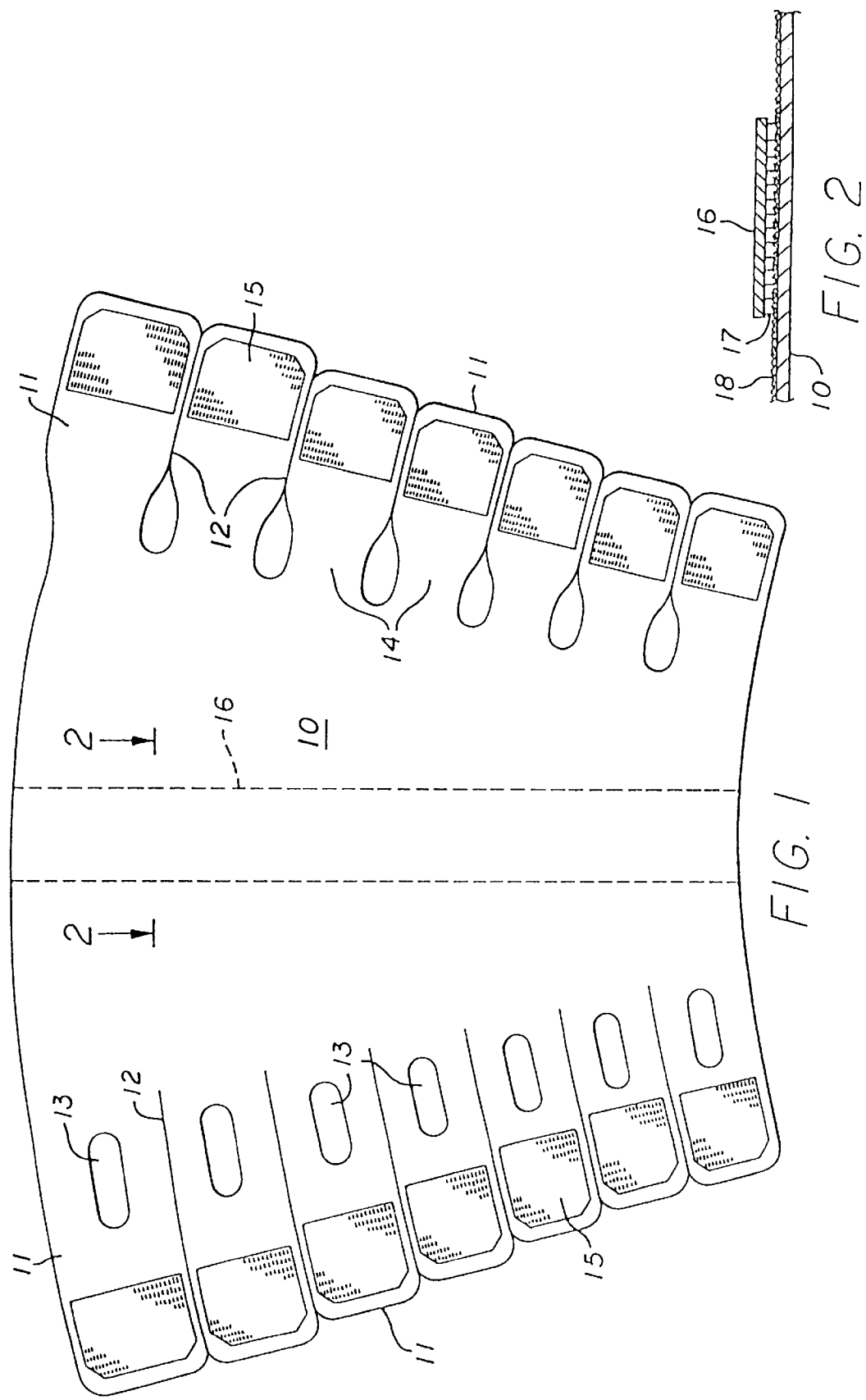

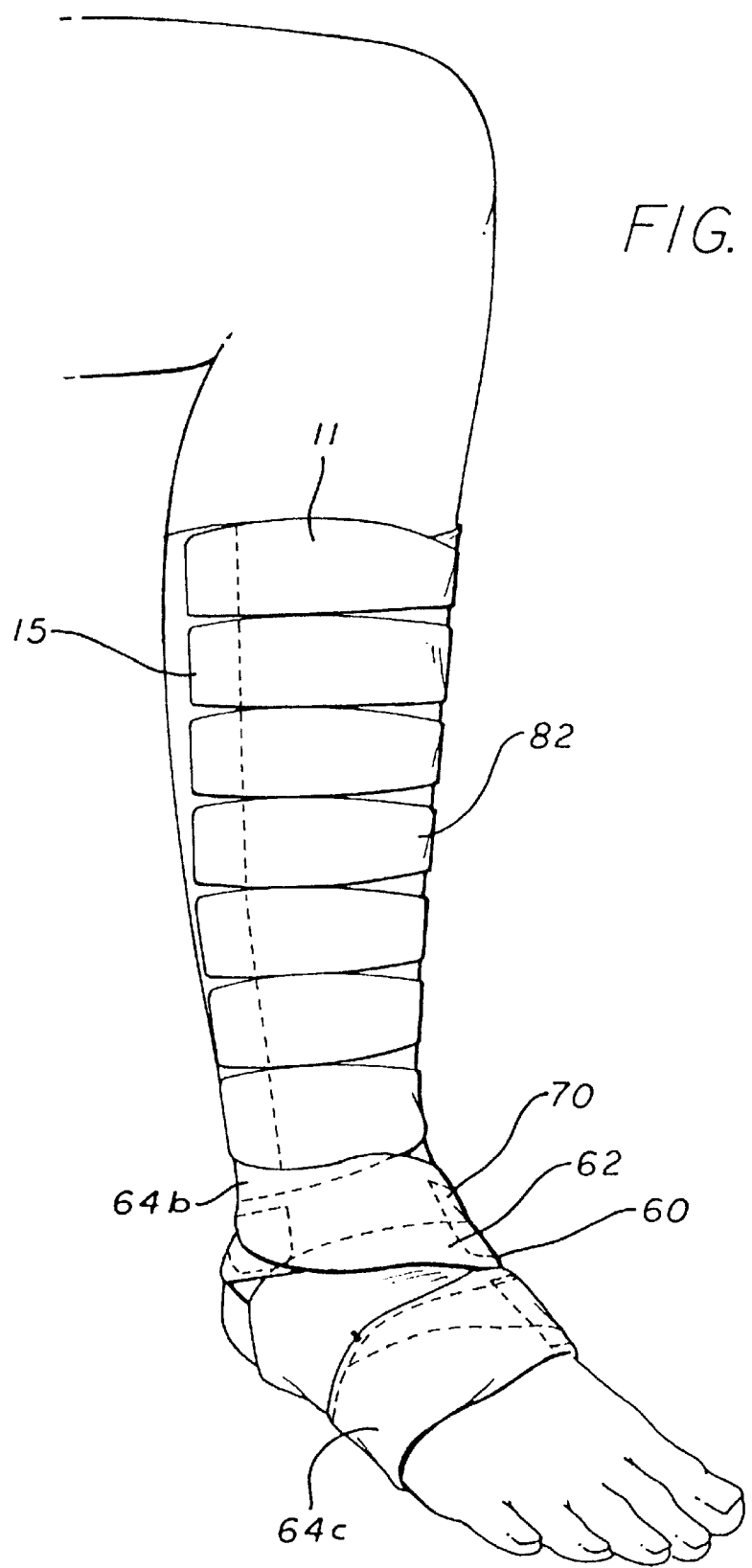

THERAPEUTIC COMPRESSION GARMENT

This application is a continuation-in-part of U.S. patent application Ser. No. 08/658,519, filed Jun. 4, 1996, now U.S. Pat. No. 5,653,244.

BACKGROUND OF THE INVENTION

This invention relates to a novel therapeutic garment for applying an adjustable, sustainable, essentially inelastic compression to a part of the body, such as a limb.

Elastic and inelastic anklets and stockings have been employed in compression therapy of the limbs. Most suffer various degrees of shortcomings, particularly in effectiveness, difficulties in application and removal, lack of adjustability, loss of compression and discomfort.

U.S. Pat. No. 3,845,769 relates to a boot having a split sleeve of essentially unyielding material shaped to fit a leg. The sleeve is held in position and compression is applied by a plurality of bands of interlocking fabric material, such as Velcro or Scotchmate.

U.S. Pat. No. 4,215,687 relates to a combination or kit which permits the in situ construction and assembly of a therapeutic compression device directly on the patient by a doctor or other skilled person. The combination or kit includes a Velcro-type anchoring tape having an interlocking fabric material on one side and a plurality of body or limb encircling Velcro-type bands which are assembled, one by one, in edge-to edge relationship either by direct contact with the anchoring tape or by indirect contract through Velcro-type splicing means. These custom-made therapeutic compression devices have achieved wide recognition in healing leg ulcers and in the treatment of lymph edema. On the other hand, the custom construction which requires splicing of the body or limb encircling bands when they are too long and when the portion of the body or limb is contoured is a tedious and time consuming task.

U.S. Pat. No. 5,120,300 relates to a compression band for use in the therapeutic device disclosed in U.S. Pat. No. 4,215,687 and, more particularly, to a compression band for quick and easy application to and removal from a body part.

U.S. Pat. No. 5,254,122 relates to a therapeutic compression device of the type disclosed in U.S. Pat. No. 4,215,687 which includes a longitudinally extending splicing band or slide fastener which facilitates quick and easy removal of the device from the body or limb and quick and easy reapplication to the body or limb without the necessity of unthreading the adjusted compression bands.

SUMMARY OF THE INVENTION

The present invention relates to a therapeutic garment for applying compression to a part of the body, such as a limb. The garment is made from a unitary piece of flexible, foldable, light weight Velcro-type loop fabric which, due to its inherent characteristics, can be prefabricated in different sizes and need not be custom-made in situ on the wearer.

The therapeutic compression garment of the present invention includes a plurality of pair of body or limb encircling bands integrally connected to a central wrap around region and extending outwardly in opposite directions from both sides of the central region to encompass the body part. Slits formed in the outer edge of the garment form a plurality of body or limb encircling bands. A slot in one of the bands in each pair accommodates the opposite band in threaded, folded relationship and Velcro-type hook surfaces on the inner surfaces at or near the ends of each pair make it possible to tighten the pairs of bands to apply the desired compression and to maintain that compression by pressing the inner hook surfaces of the band ends against the outer loop surface of the garment to anchor the bands in tightened condition.

The therapeutic garment of the present invention represents a significant advance over the custom-made therapeutic device of U.S. Pat. No. 4,215,687 in that several off-the-shelf stock sizes fit all but the very unusual limb, custom fitting is eliminated, labor and material costs are significantly reduced and the garment is less bulky, lighter in weight, more comfortable and more cosmetic.

The therapeutic garment of the present invention can be made from a single piece of flexible, foldable Velcro-type fabric having a outer loop surface. Alternatively, the central region of the garment can be equipped with a longitudinally extending slide fastener to separate portions of the one piece garment to facilitate quick removal and quick reapplication of the garment to the body part without unthreading the bands which apply the desired compression.

Because the fabric is of lighter weight and more readily flexible and foldable than the thicker, heavier and more rigid material used in the prior art custom-made therapeutic compression device described above, it is desirable to stiffen or reinforce the central region longitudinally of the garment to prevent wrinkling, collapsing or slippage of the upper portion of the garment relative to the lower portion. This can be accomplished by various suitable means, such as a narrow band of Velcro-type band having an inner hook surface which can be anchored against the outer loop surface of the garment or by a longitudinally extending flexible rod affixed to the outer surface of the central region of the garment. Use of one or more flexible rods as a reinforcement device is of particular advantage n therapeutic compression garments which extend across the knee or elbow because they will readily deflect when the knee or elbow is bent while providing the desired reinforcement.

The present invention further provides an ankle foot wrap for applying compression to the ankle and foot. The wrap is made from a flexible, foldable, light weight Velcro-type fabric having an outer loop surface. The ankle foot wrap of the present invention includes a stirrup sized for fitting the foot in the ankle foot wrap. One or more straps are anchored to one of their ends to the stirrup. Each strap has a Velcro-type hook surface positioned at the free end which is used for tightening engagement with the outer loop surface when the wearer encompasses the ankle and foot with the strap(s) to apply the desired compression and presses the hook surfaces against the outer loop surface of the ankle foot wrap to anchor the strap(s) in tightened condition.

Further provided by the present invention is a leg-ankle-foot garment for applying compression to the leg, ankle and foot. The leg-ankle-foot garment includes a leg member and an ankle foot wrap in cooperative connection with the lower edge of the leg member. The leg member comprises the therapeutic compression garment of the invention described above and adapted for the leg, which further includes a sleeve formed on the inner surface of the central region. The ankle foot wrap comprises the ankle foot wrap of the present invention described above. In use, the wearer inserts the foot into sleeve of the leg member, pulling the leg-ankle-foot garment onto the leg so that the foot slides into the stirrup of the ankle foot wrap. The leg-ankle-foot garment is a significant advance over previous custom made devices in that the sleeve makes the therapeutic leg-ankle-foot garment significantly easier to apply and remove than would be possible if the leg member and ankle-foot-wrap were separately applied. Having the ankle-foot wrap conjoined in cooperative connection to the leg member significantly improves the convenience of putting the device on while providing therapeutic compression at least equivalent to that of the leg member and the ankle-foot wrap worn together but applied separately.

For a more complete understanding of the present invention reference can be made to the detailed description which follows and to the accompanying drawings.

DESCRIPTION OF THE DRAWINGS

FIG. 1 is a view of the inner surface of a therapeutic compression garment of the present invention;

FIG. 2 is a sectional view taken along the line 2—2 of FIG. 1 looking in the direction of the arrows;

FIG. 13 is a view of the ankle-foot-leg garment in place on a wearer.

DESCRIPTION OF PREFERRED EMBODIMENTS

Figure 3:
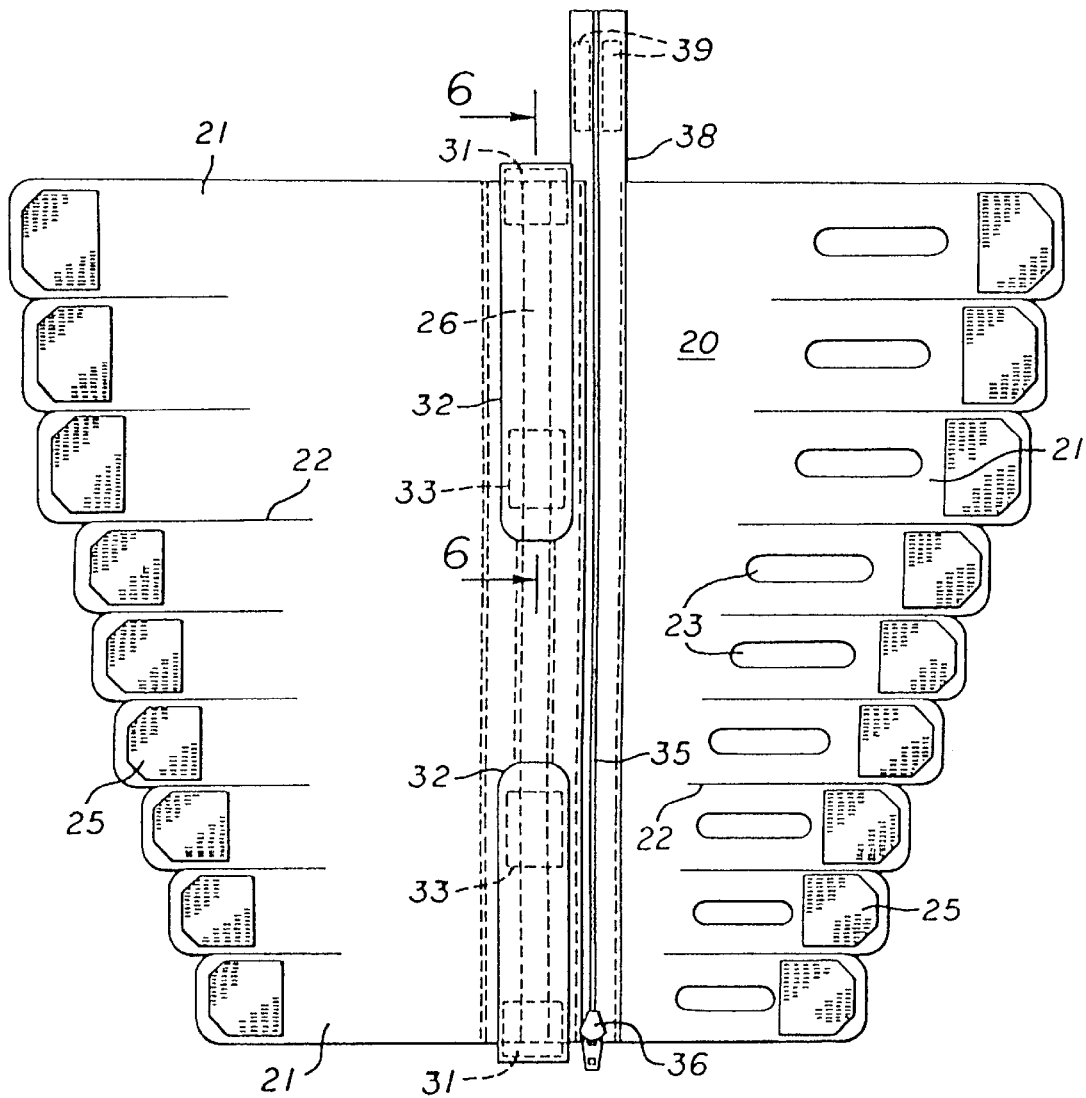
FIG. 3 is a view of the inner surface of another embodiment of the therapeutic compression garment of the present invention.

The therapeutic compression garment shown in FIG. 1 is made in one piece as a unitary construction from a flexible, foldable Velcro-type fabric having an outer loop surface which is preferably a light weight loop fabric of the type designated Velcro 3610 or Velcro 3800, the former being substantially inelastic and the latter having a limited stretch at least in the vertical or longitudinal direction.

The therapeutic garment of FIG. 1 includes a central region 10 which is wrapped around the body part. Slits 12 are formed in the outer edge and extend from the outer edge toward the central region. The slits form a plurality of pairs of bands 11 integrally connected to the central region and extending outwardly in opposite directions from both sides of the central region to encompass the body part. Accordingly, the bands 11 are defined by slits 12. One of the bands of each pair includes a slot 13 to accommodate the opposite band in threaded, folded relationship to apply compression to the body part encompassed by the garment. The bands which are threaded through the slots 13 may include portions 14 of reduced width formed by widening the slits separating the bands, but such narrow width portions are not essential because of the flexible, foldable characteristics of the fabric. The inner surfaces of the bands have Velcro-type hook surfaces 15 at or near their ends. The opposite bands of each pair are extended toward each other and one band of each pair is threaded through the slot in the other band of the pair and then tightened to apply the desired compression to the body part. The inner hook surfaces 15 are then pressed against the outer loop surface 18 of the fabric to anchor the bands in tightened condition. The garment is removed by separating the hook surfaces 15 of the bands from the outer loop surface of the garment and then unthreading the bands.

In order to facilitate handling the fabric during application to the body part and to prevent wrinkling of the fabric or slippage of the upper end of the garment relative to the lower end, the fabric is preferably stiffened or reinforced longitudinally, such as by a strip, rod or other suitable means. In the therapeutic garment shown in FIG. 1 and as best shown in FIG. 2, such reinforcement is provided by a longitudinally band 16 of Velcro-type fabric having an inner hook surface 17 which adheres to the outer loop surface 18 of the garment. The strip is preferably a high shear hook tape, such as Velcro P87 affixed along the vertical center line of the central region 10 of the garment to stiffen it and prevent possible wrinkling.

The therapeutic garment of this invention does not have to be custom-made to the body part because the fabric readily conforms to the body contour due to its inherent characteristics, such as light weight, flexibility and foldability, in contrast to the heavier, thicker and more rigid materials used in the therapeutic device described in U.S. Pat. No. 4,215,687. In the therapeutic garment of the present invention, some overlap of the bands can be tolerated without creating gaps or spaces n the compression applied to the body part. The Velcro knitloop 3800 fabric is particularly advantageous in that its limited stretch characteristics permit it to shape, mold and conform to the body particularly in the knee and elbow regions, while applying an inelastic compression to the body part due to the fact that the stretch limit is exceed in tightening the bands before the desired compression levels are reached. The Velcro knit loop 3800 fabric is a nylon multifilament yarn of 28 gage knit construction having specifications as follows: weight: 9.70 oz. per sq. yd.; thickness: 0.060 inches; peel strength (w/hook 88): 1.30 plw; shear strength (w/hook 88): 27.49 psi; tension strength (w/hook 88): 10.56 psi; break strength (machine direction): 69.1 lbs; shrinkage: 3% max; curl: 6.25% max; stiffness: 2.5 inch min.; fabric stretch for 5 lb. force applied to band: 5.5% I the cross machine or longitudinal direction of garment and 2.5% in the machine or horizontal direction of the garment. The fabric is oriented in the garment such that the greater strength is in the longitudinal or vertical direction of the garment and the lesser stretch is in the transverse or horizontal direction of the garment.

In the therapeutic compression garment shown in FIG. 1 for use on a log above or below the knee and made of a relatively inelastic material, such as Velcro 3610 loop fabric, the central region 10 is wide at the top than at the bottom and the pairs of limb compression bands are longer at the top than the pairs of limb compression bands at the bottom. The pairs of limb compression bands are separated from adjacent pairs of limb compression bands by slits which extend downwardly in opposite directions at angles of about 15°+/− 10% from the longitudinal middle of the central region to minimize the overlap of the compression band applied to the leg. The garment can be shortened longitudinally by cutting off upper or lower pairs of bands.

Figure 4:
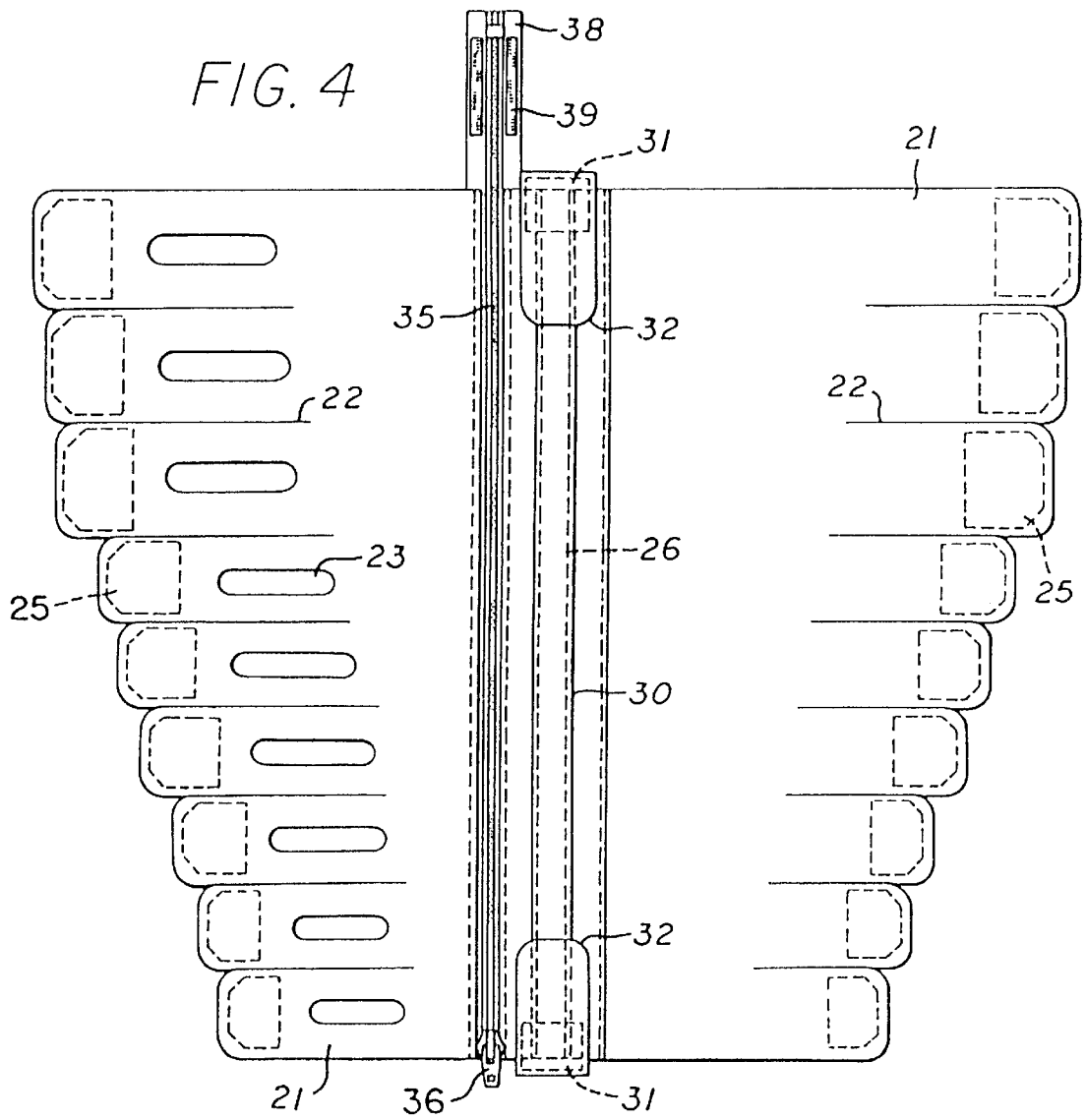
FIG. 4 is a view of the outer surface of the therapeutic compression garment shown in FIG. 3.
Figure 6:
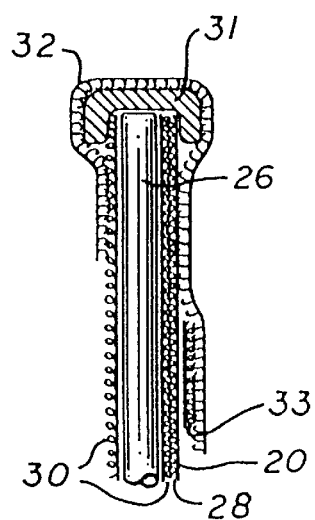
FIG. 6 is cross-sectional view taken along the line 6—6 of FIG. 3 looking in the direction of the arrows.
Figure 7:
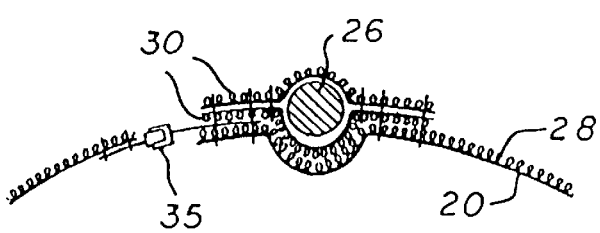
FIG. 7 is a view taken along the line 7—7 of FIG. 5 looking in the direction of the arrows.

The therapeutic compression garment of FIGS. 3 and 4 is preferably made of a limited stretch fabric, such as Velcro 3800 loop fabric, having an outer loop surface 28 (see FIGS. 6 and 7). The fabric is oriented in the garment with the greater stretch in the longitudinal direction and the lesser stretch in the transverse direction. The garment has a central region 20 for wrapping partially around the body part and a plurality of pairs of bands 21 integrally connected to the central region and extending outwardly in opposite directions from both sides of the central region to encompass the body part. The bands 21 are defined by parallel slits 22 which are arranged at about 90° from the longitudinal direction of the garment. Transversely extending slots 23 are provided in one of the bands of each pair to accommodate the opposite band in threaded, folded relationship, and Velcro-type hook surfaces 25 are carried at the ends or near the ends on the inner surfaces of each pair of bands.

In applying the therapeutic compression garment on a body part, such as a region extending from above the knee to the ankle, the opposite bands of each pair are extended toward each other and one band of each pair is threaded through a slot in the other band of the pair and then tightened to apply the desired compression. The inner hook surfaces are pressed against the outer loop surface of the garment to anchor the bands in tightened condition.

In order to stiffen or reinforce the garment and prevent it from collapsing or wrinkling during application, a longitudinal bandable or flexible rod is mounted against the outer surface of the garment as shown in FIG. 7. The rod, for example, a cylindrical silicon rubber rod, is accommodated in a picket 30 having an outer loop surface sewn to the outer loop surface 28 of the central region 20 of the garment. To prevent irritation to the skin of the wearer of the garment, a cushioning pad 31 is held in place at each end of the rod 26 by suitable means, such as a strip 32 of Velcro-type fabric having an inner hook surface which adheres at one end to the outer loop surface 28 of the garment and at the other end to a patch of loop surface material 33 fixed to the inner surface of the garment.

A longitudinally extending slide fastener or zipper 35 extends at least the longitudinal length of the central region 20 of the garment to facilitate removal and reapplication of the garment without unfastening the bands. In the therapeutic compression device shown in FIGS. 3 and 4 for use on a leg, the runner 36 closes the slide fastener during its longitudinal movement from the upper end of the garment to the lower end of the garment and opens the slide fastener during its upward return movement. When the garment is applied to an arm, the direction of the closure of the runner 36 is reversed because starting the zipper closure requires both hands, and it would be virtually impossible to attach and start the zipper at the top of the arm.

Figure 5:
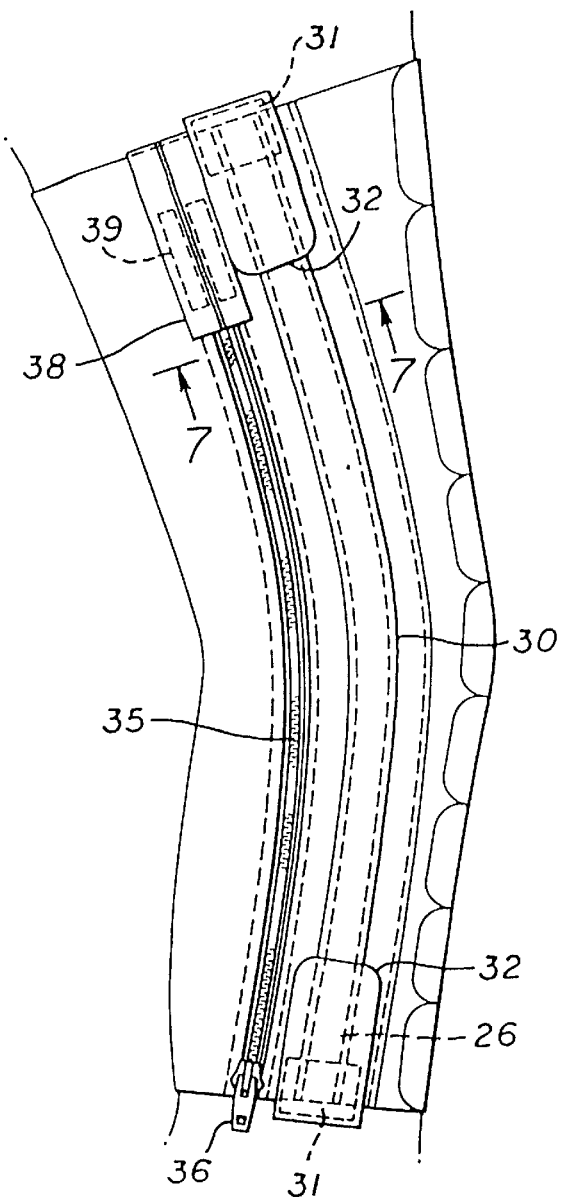
FIG. 5 is a view of the therapeutic compression garment shown in FIGS. 3 and 4 applied to a leg.

In the preferred embodiment of the therapeutic compression garment shown in FIGS. 3 and 4, the slide fastener extends at one end beyond the upper or lower end of the central region of the garment to permit separation of the central region along its entire length while the separated portions of the central region remain connected by the extreme end of the extended portion of the slide fastener. The extended portion 38 shown in FIG. 3 permits the runner 36 to side upwardly to open the slide fastener beyond the upper edge of the central region of the garment to facilitate removal of the garment from the body part and reapplication thereof. In this way, the garment can be removed and replaced by loosening and without unthreading the compression bands. The upward movement of the slide 36 is limited so that the separated portions of the central region of the garment remain connected by the end of the extended portion of the slide fastener. The extension 38 has a strip of hook tape 39 along each of its outer cloth edges to hold it against the outer loop surface of the garment in its folded down position shown in FIG. 5.

A flap (not shown) may be proved to cover the slide fastener and the folded down zipper extension 38. If provided, the strips 39 of hook tape can be omitted. In the alternative, the outer surface of the flap can be provided with a Velcro-type loop surface and the extension 38 and the hook surface strips can be folded over the flap and adhered thereto. The flap would contribute to the needed stiffening and wrinkling resistance provided by the longitudinally extending rod 26.

The therapeutic compression garment shown in FIGS. 3 and 4 equipped with a longitudinally extending stiffening rod 26 and longitudinally extending slide fastener 35 would preferably be worn such that the stiffening rod and slide fastener are located on the inside or outside of a limb to facilitate opening and closing the slide fastener and to prevent the stiffening rod from interfering with the bending of the knee or elbow. In this way, the stiffening rod flexes with the bending of the knee or elbow without undue wrinkling or distortion of the garment.

Sleeve

Figure 8:
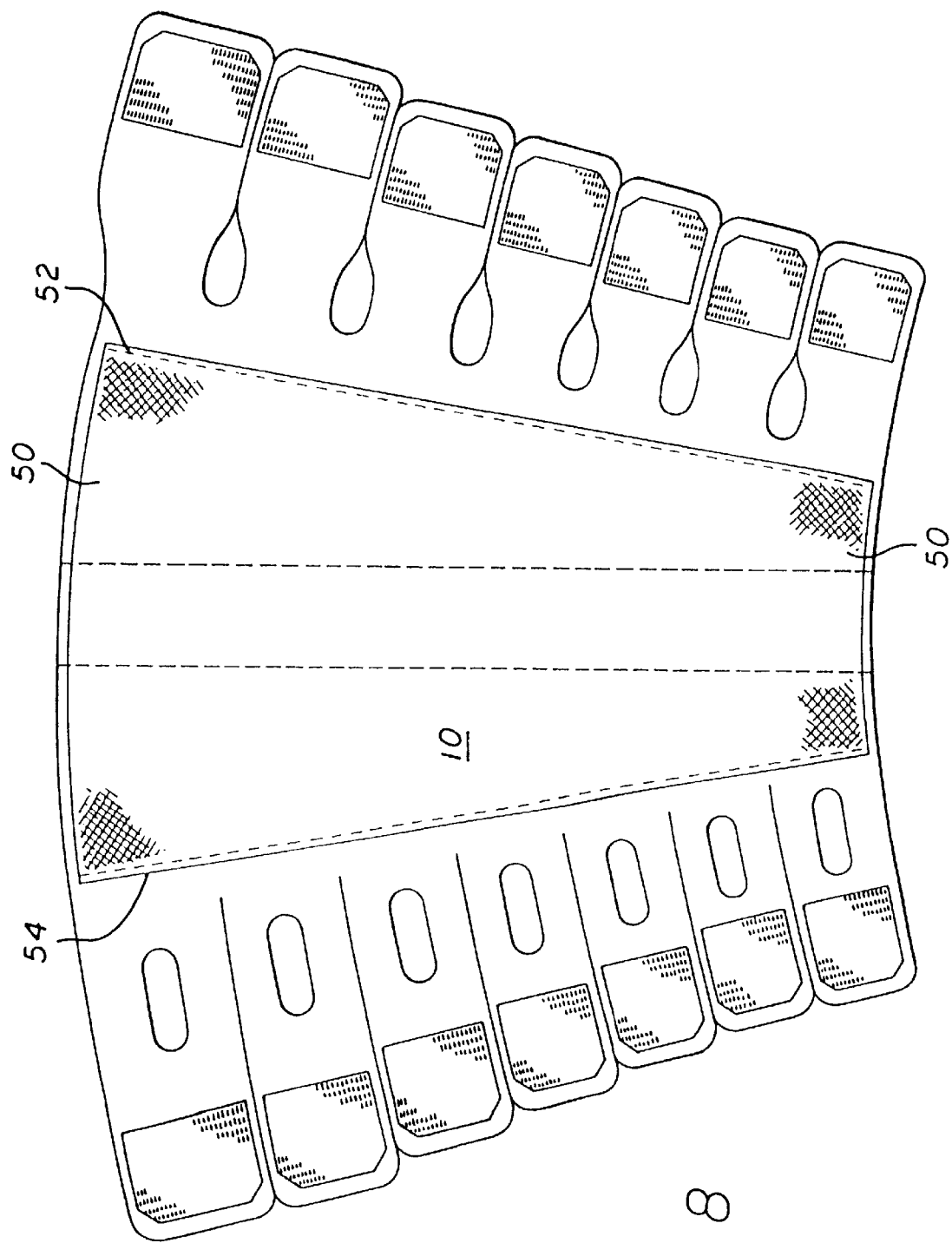
FIG. 8 is a view of the inner surface of a therapeutic compression garment of the present invention showing the sleeve.

In order to facilitate fitting or slipping-on the therapeutic garment, a longitudinally oriented sleeve 50 is formed from the inner surface of the central region (FIG. 8). The sleeve extends substantially the length of the garment. The sleeve can be formed from a sheet of fabric whose lateral edges 52, 54 are attached to the inner surface of the central region. A sleeve could also be formed from an essentially cylindrically formed fabric, such as a sock or tube, which could be attached at its edges when positioned on the flat inner surface of the central region.

The sheet or tube of fabric can be formed from an elastic mesh fabric or other like fabric in order to slip-on over the heel of the foot in the case of a garment adapted for the leg, or to slip-on over the hand for a garment adapted for the arm of the wearer. Elastic mesh fabric or the like provides a comfortable and breathable fabric. Attachment of the fabric to the inner surfaces of the therapeutic garment 10 can be achieved by sewing, gluing, welding or other methods well known in the art for attaching fabrics to each other. The sleeve 50 maintains the ordered parallel arrangement of the garment's limb encircling bands 11. The sleeve 50 makes the therapeutic garment 10 significantly easier to apply and remove than would be possible with a sleeveless embodiment of the garment 10 (FIG. 1), thereby overcoming an obstacle to patient compliance.

Ankle-Foot Wrap

Figure 9:
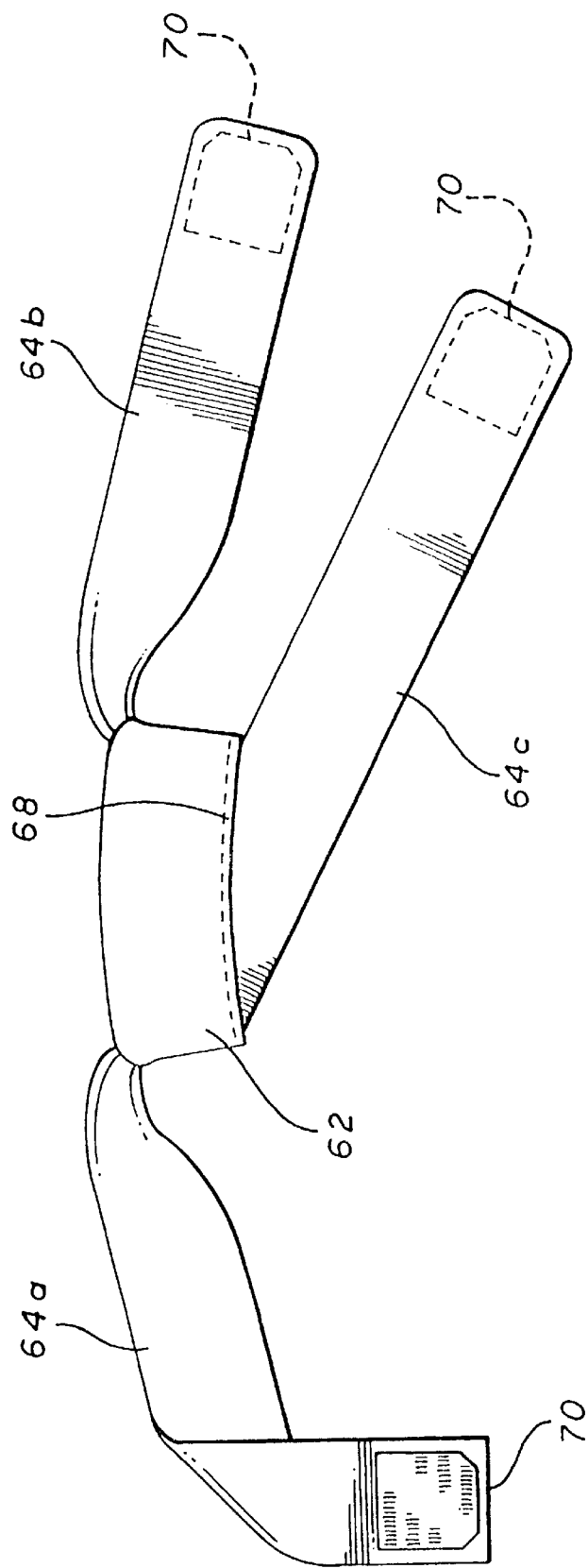
FIG. 9 is a view of the ankle foot wrap.
Figure 10:
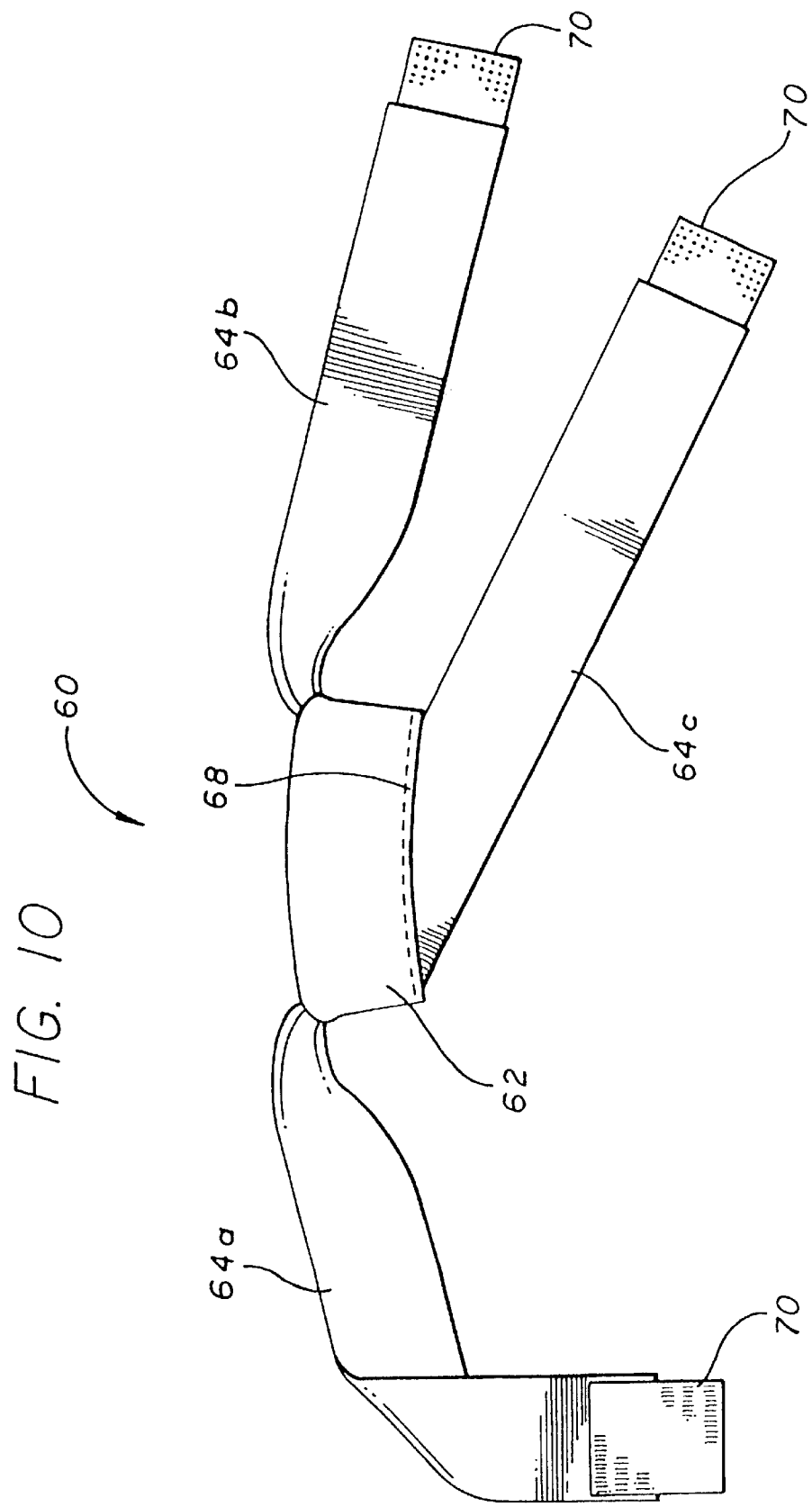
FIG. 10 is a view of the ankle foot wrap having detachable Velcro-hook type surfaces at the free ends of the straps.

As shown in FIGS. 9 and 10, an ankle-foot wrap 60 is made of an essentially pliant, non-elastic, limited stretch fabric having a Velcro-type loop outer surface and an inner surface which, for the most part, is smooth. A preferred material is Velcro brand Velstretch.

The ankle-foot wrap 60 includes a stirrup 62 shaped for fitting the wearer's foot into the ankle-foot wrap 60. The stirrup 62 is shaped as a flat-based loop for receiving the wearer's foot so that the stirrup encircles the bottom and top of the foot in an area between the toes and the ankle. The stirrup 62 positions the ankle-foot wrap 60 on the foot and functions as an anchor for the ankle and foot encircling straps 64 (i.e 64a, b, c) which serve as compression bands. The width of the stirrup material encircling the foot can be from about 1 inch to about 4 inches, and is preferably about 2 inches.

Attached or anchored to the stirrup 62 are one or more straps 64 which are wrap-around foot and ankle compression bands extending outwardly. In the case of a plurality of straps 64a, b, c, they can extend in the same or opposite directions from the stirrup 62. It will be understood that the straps can be anchored to the stirrup at various angles in order to achieve efficient and convenient wrapping of the ankle and/or foot. A strap 64 is a long narrow strip of pliant material (e.g. Velcro-type material described above) anchored at one end to the stirrup 62, with the other end being free. In a preferred arrangement, a pair of straps 64a, 64b is anchored to the stirrup such that the free ends of the straps extend rearwardly. In use, the wearer pulls on the rearward extending straps 64, 64b in order to pull the ankle foot wrap 60 into a desired position on the wearer's foot. Once in position, the rearward extending straps 64a, 64b are wrapped around the ankle to apply compression. As shown in FIG. 10, a forwardly extending strap 64c is attached to the forward edge 68 of the stirrup. The width of a strap can be from about 1 inch to about 4 inches, and are preferably about 2 inches in width. The length of a strap can be adjusted to a desired length, and can be from about 3 inches to about 36 inches in length, and typically about 16 inches long. As shown in FIG. 10, the Velcro-type hood surface 70 can be detachably positioned to the free end of a strap. By detaching the Velcro-type hook surface and cutting the strap and re-attaching the hook surface to the new free end of the strap, the strap band can be adjusted to the desired length for the user.

For an ankle-foot wrap having a plurality of straps (i.e compression bands), the widths of the straps are not necessarily the same, nor are the lengths. The ankle-foot wrap employs widths and lengths of straps adapted for the wearer's shape and size or other idiosyncracies.

Figure 11:
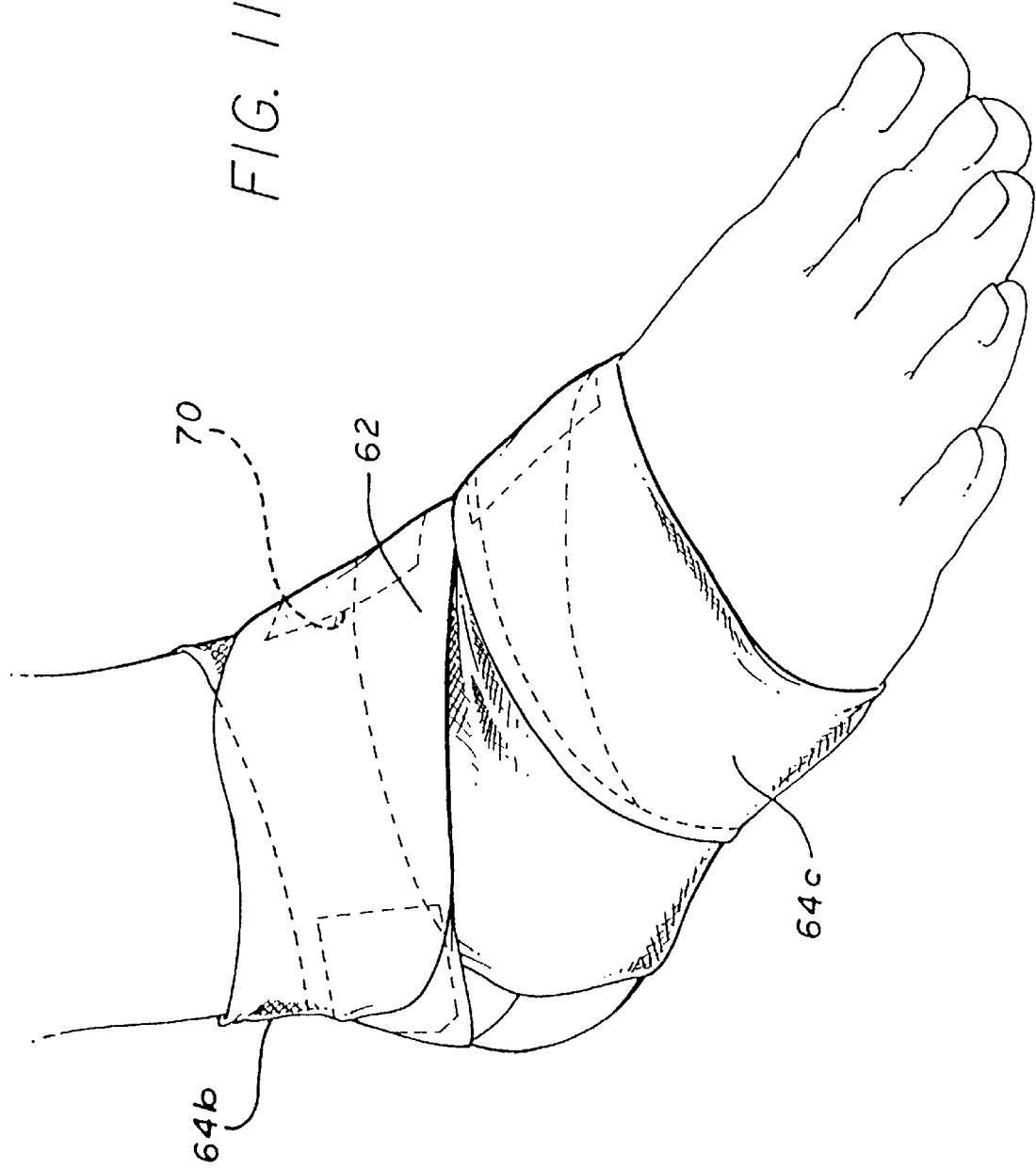
FIG. 11 is a view of the ankle foot wrap in use around the wearer's foot.

Referring to FIG. 11, the strap 64a or 64b used to apply compression around the ankle extends rearwardly, whereas the strap 64c used to apply compression around the sole of the foot extends forwardly toward the undersideof the foot. A Velcro-type hook surface 70 at or near the free end of each strap functions for tightening engagement with the outer loop surface of the ankle-foot wrap. Thus, the Velcro-type hook surface 70 makes it possible to tighten or loosen the straps 64 to apply the desired compression and to maintain that compression by pressing the inner hook surface 70 of the strap ends against the outer loop surface of the ankle-foot wrap 60 to anchor the straps 64 in tightened condition. In this way, the straps 64 are used to apply compression, permitting the wearer to wrap around the ankle or foot with ease and flexibilty to accomodate any size or shape of either the ankle or foot, thereby applying and maintaining non-elastic pressure conforming to the concavities of the ankle joint and foot.

Leg-Ankle-Foot Garment

Figure 12:
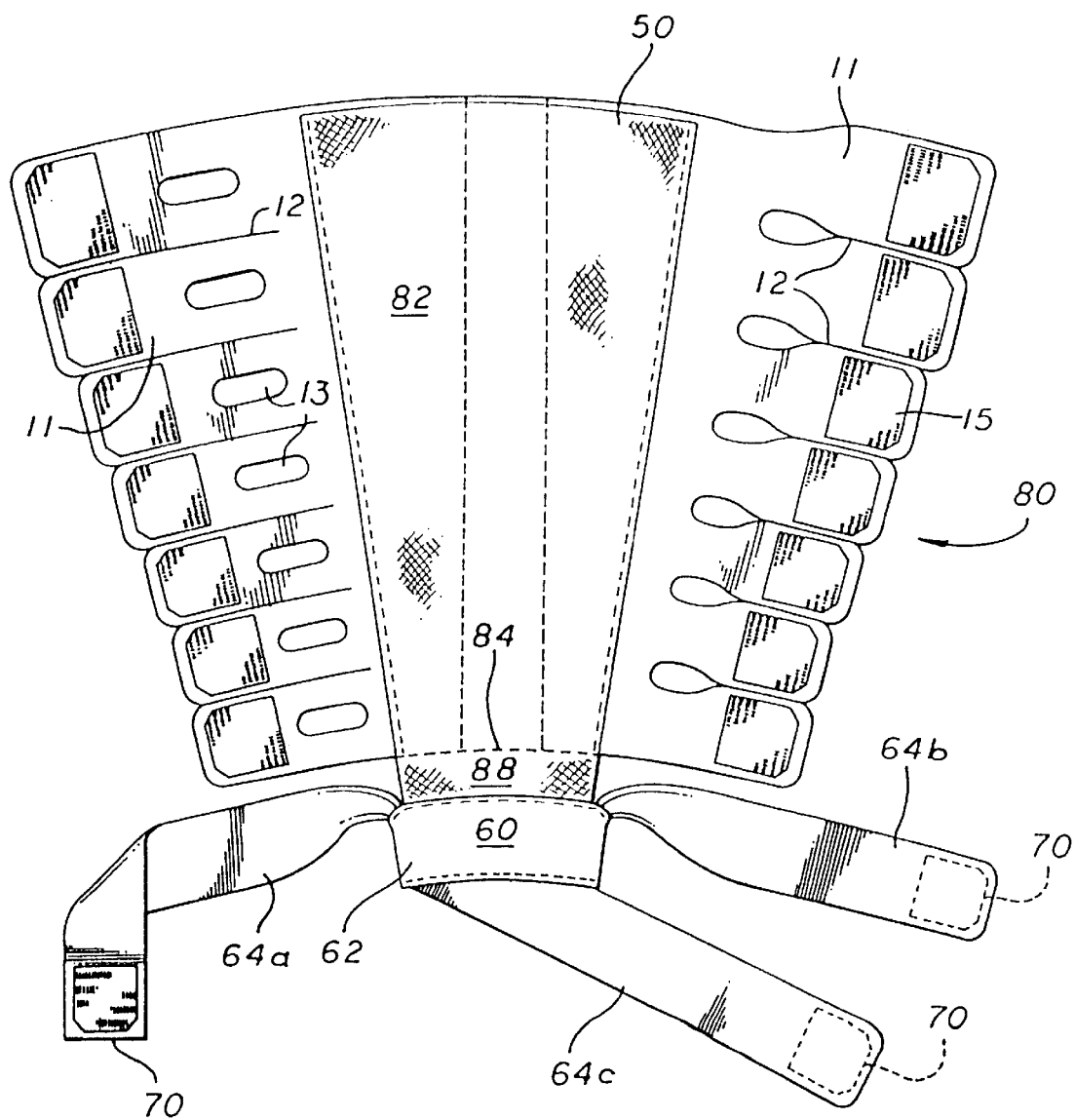
FIG. 12 is a view of the inner surface of the ankle-foot-leg garment.

As shown in FIG. 12, a further embodiment of the present invention provides a thereapeutic garment 80 for applying a controlled level of non-elastic compression to the leg, ankle and foot by effectively combining the non-elastic limb encircling therapeutic compression garment (FIGS. 1 and 8) adapted for the leg, i.e. a leg member, described above with an ankle-foot wrap compression device 60 (FIGS. 9 and 10). The term "leg-ankle-foot" garment 80 as used herein refers to the combination of a leg member 82 which refers to the non-elastic limb encircling compression garment (FIGS. 1, 8) adapted for the leg and the ankle-foot wrap compression device (FIGS. 9, 10), as set forth in detail below.

The leg-ankle-foot garment 80 has the advantage of providing sustained compression over the leg, ankle and foot. The leg-ankle-foot garment permits the wearer to easily apply and remove the garment and to comfortably maintain a controlled level of non-elastic compression that is readily adjustable with minimal effort. The leg-ankle-foot garment 80 effectively applies compression pressure to the concavities and joints around the ankle and foot (FIG. 13) and functions to maintain that compression around the leg, ankle and foot significantly easier than with previous devices.

The leg-ankle-foot garment 80 includes a leg member 82 which is a therapeutic garment of the present invention adapted for the leg conjoined to an ankle-foot wrap 60. As used in the context of the leg-ankle-foot garment 80, the term "leg member" refers to a therapeutic garment adapted for the leg. By "conjoined" is meant a functionally cooperative association or attachment between the leg member 82 and the ankle-foot wrap 60.

The leg member 82 is formed from a unitary piece of fabric and includes a plurality of pair of body or limb encircling bands 11 integrally connected to a central wrap around region 10 and extending outwardly in opposite directions from both sides of the central region 10 to encompass the body part. Slits 12 formed in the outer edge of the leg member and extending into the central region 10 form a plurality of bands 11. A slot 13 in one of the bands 11 in each pair accommodates the opposite band in threaded, folded relationship and Velcro-type hook surfaces 15 on the inner surfaces at or near the ends of each pair make it possible to tighten the pairs of bands 11 to apply the desired compression and to maintain that compression by pressing the inner hook surfaces 15 of the band ends against the outer loop surface of the leg member 80 to anchor the bands in tightened condition.

The ankle-foot wrap 60 is flexibly attached to the lower edge 84 of the central region 10 of the leg member. The inner surface of the leg member 80 includes a sleeve 50 which can be formed from a sheet of fabric whose lateral edges 52, 54 are attached to the inner surface. In one embodiment, the front surface of the sleeve 50 extends below the lower edge 84 of the central region 10 for attaching the ankle-foot wrap 60 to the leg member 82, the fabric 88 extending sufficiently below the lower edge 84 of the central region 10 for attachment of its edges to the inner smooth surface of the stirrup 62. The sheet of fabric forming the sleeve 50 can be an elastic mesh fabric or other like fabric in order to slip-on over the heel of the foot and to provide a comfortable and breathable fabric. Attachment of the fabric forming the sleeve 50 to the inner surfaces of the leg member 82 or the ankle-foot wrap 60 can be achieved by sewing, gluing, welding or other methods well known in the art for attaching fabrics to each other. In a preferred attachment of the ankle-foot wrap 60 to the leg member 82, the stirrup 62 is advantageously positioned to be centered to the vertical axis of the leg member.

In combination with the inner surface of the leg member 82 and the inner smooth surface of the stirrup 62, the sleeve 50 makes it easier for the a wearer to slip the leg-ankle-foot garment over the foot, ankle and onto the leg. The sleeve 50 maintains the ordered parallel arrangement of the leg member's limb encircling bands 11. The sleeve 50 also maintains an ordered position or configuration of the leg member 82 in relation to the ankle foot wrap 60. The sleeve 50 makes the therapeutic leg-ankle-foot garment 82 significantly easier to apply and remove than would be possible if the leg member 82 and ankle-foot-wrap 60 were separately applied. Having the ankle-foot wrap 60 conjoined to the leg member 82 significantly improves the convenience of putting the device on while providing therapeutic compression at least equivalent to that of the leg member and the ankle-foot wrap worn together but applied separately.

The present invention provides a further advantage of allowing the user to easily and rapidly adjust desired compression by adjusting the bands of the leg member or straps of the ankle-foot wrap as described above. Furthermore, embodiments of the leg-ankle foot garment equipped with a longitudinally extending slide fastener to separate portions of the leg member (as described above for the therapeutic compression garment) provide the wearer quick removal and quick reapplication of the leg-ankle-foot garment without unthreading the bands which apply the desired compression. Because of the ease of use and comfort of the leg-ankle-foot garment, the invention provides the advantage of greater patient compliance.

Therapeutic Use

In therapeutic use, a method of the invention involves treating medical disorders which require compression therapy. The method involves the step of applying to the indicated body part the garments of the invention whereby a compressive force or support is applied to the body part, such as the arm, foot, ankle and leg on subjects (human or animal) suffering from disorders that require compression therapy. Such disorders include, but are not limited to, lymphedema, phlebitis, varicose veins, burns, post-fracture and injury (including sports injury) edema, stasis ulcers, obesity and circulatory disorders requiring application of compressive devices. Compression therapy is well known in the art (H. A. Neumann and D. J. Tazzelaar, chapter on "Compression Therapy," in *Varicose Veins and Telangioectasias, Diagnosis and Treatment*, eds. John T. Bergren and Mitchell P. Goldman, Quality Med. Publ., St. Louis, 1993).

Because human skin is elastic in nature, when such systems as the lymphatic or venous return systems fail to function properly, the limb or body part accumulates fluid and stretches to accommodate edema. Under normal operation, those systems would allow that fluid to circulate and not collect in those limbs or body parts and the skin would normally accommodate only the subtle changes by expanding or contracting. Use of non-elastic compression garments of the present invention aids the skin's strength, not allowing it to stretch and accumulate fluid. The fluid must then flow through the system from the compressive force of the non-elastic compression device.

In addition, when a limb or body part is affected by poor circulation, the stagnate or poorly circulated fluid can manifest itself as ulcers. Use of compressive devices aids in that circulation. However, areas on such body parts or limbs at or near joints or concavities presents an obstacle to applying compressive devices because of the difficulties in applying and sustaining a uniform or gradient compression, which obstacles are overcome by the garments of the present invention and method of using said garments for treating such syndromes.

The invention has been shown in preferred forms and by way of example, and many variations and moficiations can be made therein within the spirit of the invention. The invention, therefore, is not intended to be limited to any specified form or embodiment, except insofar as such limitations are expressly set forth in the claims.

What is claimed is:

1. A therapeutic garment for applying compression to a part of the body comprising a unitary piece of flexible, foldable, light weight hook and loop-type fabric having an outer loop surface and an inner surface comprising a central region for wrapping partially around the body part, wherein a sleeve is formed in said central region for fitting the garment to the part of the body, and wherein slits formed in the outer edge of said garment form a plurality of bands, said plurality of pairs of bands being integrally connected to the central region and extending outwardly in opposite directions from both sides of the central region to encompass the body part, and wherein a slot formed in one of the bands of each pair accommodates the opposite band in threaded, folded relationship, and wherein hook and loop-type hook surface are positioned at the ends of the inner surfaces of each pair of band, whereby the opposite bands of each pair can be extended toward each other and one band of each pair can be threaded through the slot in the other band of the pair and tightened to apply the desired compression and their inner hook surfaces can be pressed against the outer loop surface to anchor the bands in tightened condition.

2. A therapeutic compression garment as set forth in claim 1 in which the central region is wider at the top than at the bottom and the pairs of compression bands are longer at the top than the pairs of compression bands at the bottom.

3. A therapeutic compression garment as set forth in claim 1 in which the pairs of compression bands are separated from adjacent pairs of compression bands by said slits which extend downwardly in opposite directions at angles from the longitudinally middle of the central region to minimize overlap of the compression bands applied to the body part.

4. A therapeutic compression garment as set forth in claim 1 in which the garment is substantially inelastic with a slight amount of stretch at least in the longitudinally direction of the garment.

5. A therapeutic compression garment as set forth in claim 1 in which the pairs of compression bands are separated from adjacent pairs of bands by substantially parallel slits which extend outwardly from the central region of the garment.

6. A therapeutic compression garment as set forth in claim 1 including a stiffening means extending longitudinally in the central region to prevent wrinkling and slippage of the upper end of the garment relative to the lower end when applied to the body part.

7. A therapeutic compression garment as set forth in claim 6 in which the stiffening means is a longitudinal band having a hook and loop-type hook surface adhered to the outer hook and loop-type loop surface of the garment.

8. A therapeutic compression garment as set forth in claim 6 in which the stiffening means is a longitudinal bendable rod held against the outer surface of the garment.

9. A therapeutic compression garment as set forth in claim 8 including a cushion held in place at at least one end of the rod.

10. A therapeutic compression garment as set forth in claim 1 including a longitudinally extending slide fastener in the central region of the garment to facilitate removal from or reapplication to the body part without undoing the bands.

11. A therapeutic compression garment as set forth in claim 10 in which at least one end of the slide fastener extends beyond the central region of the garment to permit separation of the central region along its entire length while the separated portions of the central region remain connected by the extended portion of the slide fastener.

12. A therapeutic compression garment as set forth in claim 11 including means for holding the extended portion of the slide fastener in folded down position against the outer surface of the garment.

13. A therapeutic compression garment as set forth in claim 10 including a flap covering the slide fastener.

14. An ankle-foot wrap for applying compression to the ankle and foot comprising a flexible, foldable, light weight hook and loop-type fabric having an outer loop surface, said wrap comprising:

(a) an annular stirrup sized for fitting the foot in the wrap;

(b) one or more straps anchored at one end to the stirrup for encompassing the ankle and foot, each strap having a hook and loop-type hook surface positioned at the free end of each strap for tightening engagement with the outer loop surface whereby said one or more straps are wrapped around the foot and ankle to apply the desired compression and their hook surfaces pressed against the outer loop surface to anchor said one or more straps in tightened condition.

15. The ankle foot wrap of claim 14 having three straps.

16. The ankle foot wrap of claim 14 wherein said hook and loop-type hook surface positioned at the free end of said one or more straps is detachable.

17. A leg-ankle-foot garment for applying compression to the leg, ankle and foot comprising a flexible, foldable, light weight hook and loop-type fabric having an outer loop surface and an inner surface, said garment comprising:

(a) a leg member comprising a unitary piece of flexible, foldable, light weight hook and loop-type fabric having an outer loop surface and an inner surface comprising a central region for wrapping partially around the body part, wherein a sleeve is formed in said central region for fitting the garment to the part of the body, and wherein slits formed in the outer edge of said garment form a plurality of bands, said plurality of pairs of bands being integrally connected to the central region and extending outwardly in opposite directions from both sides of the central region to encompass the body part, and wherein a slot formed in one of the bands of each pair accommodates the opposite band in threaded, folded relationship, and wherein hook and loop-type hook surface are positioned at the ends of the inner surfaces of each pair of band, whereby the opposite bands of each pair can be extended toward each other and one band of each pair can be threaded through the slot in the other band of the pair and tightened to apply the desired compression and their inner hook surfaces can be pressed against the outer loop surface to anchor the bands in tightened condition; and (b) an ankle-foot wrap for applying compression to the ankle and foot, said wrap in cooperative connection with the lower edge of the leg member, said wrap comprising i. an annular stirrup sized for close-fitting the foot in the wrap;

ii. one or more straps anchored at one end to the stirrup for encompassing the ankle and foot, each strap having a hook and loop-type hook surface positioned at the free end of each strap for tightening engagement with the outer loop surface whereby said one or more straps are wrapped around the foot and ankle to apply the desired compression and their hook surfaces pressed against the outer loop surface to anchor said one or more straps in tightened condition.

18. The leg-ankle-foot garment as set forth in claim 17 in which the central region is wider at the top than at the bottom and the pairs of compression bands are longer at the top than the pairs of compression bands at the bottom.

19. The leg-ankle-foot garment as set forth in claim 17 in which the pairs of compression bands are separated from adjacent pairs of compression bands by said slits which extend downwardly in opposite directions at angles from the longitudinally middle of the central region to minimize overlap of the compression bands applied to the body part.

20. The leg-ankle-foot garment as set forth in claim 17 in which the garment is substantially inelastic with a slight amount of stretch at least in the longitudinally direction of the garment.

21. The leg-ankle-foot garment as set forth in claim 17 in which the pairs of compression bands are separated from adjacent pairs of bands by substantially parallel slits which extend outwardly from the central region of the garment.

22. The leg-ankle-foot garment as set forth in claim 17 including a stiffening means extending longitudinally in the central region to prevent wrinkling and slippage of the upper end of the garment relative to the lower end when applied to the body part.

23. The leg-ankle-foot garment as set forth in claim 22 in which the stiffening means is a longitudinal band having a hook and loop-type hook surface adhered to the outer hook and loop-type loop surface of the garment.

24. The leg-ankle-foot garment as set forth in claim 22 in which the stiffening means is a longitudinal bendable rod held against the outer surface of the garment.

25. The leg-ankle-foot garment as set forth in claim 24 including a cushion held in place at at least one end of the rod.

26. The leg-ankle-foot garment as set forth in claim 17 including a longitudinally extending slide fastener in the central region of the garment to facilitate removal from or reapplication to the body part without undoing the bands.

27. The leg-ankle-foot garment as set forth in claim 26 in which at least one end of the slide fastener extends beyond the central region of the garment to permit separation of the central region along its entire length while the separated portions of the central region remain connected by the extended portion of the slide fastener.

28. The leg-ankle-foot garment as set forth in claim 27 including means for holding the extended portion of the slide fastener in folded down position against the outer surface of the garment.

29. The leg-ankle-foot garment as set forth in claim 26 including a flap covering the slide fastener.

30. The leg-ankle-foot-leg garment of claim 17 having three straps.

31. The leg-ankle-foot-leg garment of claim 17 wherein said hook and loop-type hook surface positioned at the free end of said one or more straps is detachable.

32. A method for treating medical disorder which require compression therapy, the method comprising the step of applying to the indicated body part the garment of claim 1, 14, or 17.

33. The method of claim 32 wherein said medical disorder is selected from the group consisting of lymphedema, phelibitis, varicose veins, post-fracture and injury edema, stasis ulcers, obesity, and circulatory disorders.

* * * * *